United States Patent [19]
Karrer et al.

[11] Patent Number: 5,324,695
[45] Date of Patent: Jun. 28, 1994

[54] REGENERATION OF METAL OXIDE CATALYSTS

[75] Inventors: Lothar Karrer, Pfungstadt; Klaus Herzog, Ludwigshafen; Heinrich Aichinger, Mannheim, all of Fed. Rep. of Germany; Hans-Dieter Eichhorn, Cleveland, United Kingdom; Guenter Herrmann, Heidelberg, Fed. Rep. of Germany

[73] Assignee: BASF Aktiengesellschaft, Ludwigshafen, Fed. Rep. of Germany

[21] Appl. No.: 2,415

[22] Filed: Jan. 8, 1993

[30] Foreign Application Priority Data

Jan. 8, 1992 [DE] Fed. Rep. of Germany ....... 4200248

[51] Int. Cl.$^5$ .................. B01J 23/94; B01J 23/92; B01J 38/60; C07C 2/68
[52] U.S. Cl. ........................ 502/27; 502/26; 502/28; 585/462; 585/467
[58] Field of Search .............. 502/24, 26, 27, 28

[56] References Cited

U.S. PATENT DOCUMENTS

| | | | |
|---|---|---|---|
| 2,585,033 | 2/1952 | Pitzer | 502/27 |
| 2,605,235 | 7/1952 | Pitzer | 502/24 |
| 4,049,575 | 9/1977 | Sasaki et al. | 252/439 |
| 4,162,234 | 7/1979 | Grasselli et al. | 252/452 |
| 4,330,429 | 5/1982 | Sasaki et al. | 585/626 |
| 4,410,450 | 10/1983 | Sasaki et al. | 502/27 |
| 4,419,267 | 12/1985 | Sasaki et al. | 502/26 |
| 4,609,635 | 9/1986 | Cahavest et al. | 502/26 |

FOREIGN PATENT DOCUMENTS

| | | |
|---|---|---|
| 452630 | 10/1991 | European Pat. Off. . |
| 2530959 | 2/1976 | Fed. Rep. of Germany . |
| 2560480 | 2/1976 | Fed. Rep. of Germany . |
| 2848850 | 5/1979 | Fed. Rep. of Germany . |
| 204409 | 11/1983 | Fed. Rep. of Germany . |
| 271997 | 9/1989 | Netherlands . |

*Primary Examiner*—Paul E. Konopka
*Attorney, Agent, or Firm*—Keil & Weinkauf

[57] ABSTRACT

A process for regenerating deactivated metal oxide catalysts comprising at least one of the elements antimony, iron, bismuth, molybdenum, vanadium, tungsten and/or uranium and a peptizable carrier, comprises the steps of:
a) grinding the metal oxide catalyst in the presence of water to a particle size of from 10 nm to 10 μm,
b) heating the aqueous suspension of the metal oxide catalyst of stage a) to 30–100° C. and adding an acid which peptizes the carrier,
c) spray drying the acidic suspension of the metal oxide catalyst,
d) heating the fluidizable metal oxide catalyst particles of stage c) to 500°–850° C.

11 Claims, No Drawings

REGENERATION OF METAL OXIDE CATALYSTS

The present invention concerns a process for regenerating deactivated metal oxide catalysts comprising at least one of the elements antimony, iron, bismuth, molybdenum, vanadium, tungsten and/or uranium and also peptizable carriers.

Metal oxide catalysts used in fluidized bed form in the oxidation of propene to acrolein or in the amoxidation of propene to acrylonitrile undergo deactivation in the course of the reaction and are comminuted by the mechanical stress, so that their fluidizability is impaired. Some of the catalyst particles are carried away by the reaction gases and when recovered are found to be contaminated by organics and inorganics.

DE-C-25 60 480 discloses a process for regenerating deactivated metal oxide catalysts containing an oxide of antimony and at least one of the metals iron, cobalt, nickel, manganese, uranium, zinc and copper and as additional component one of the oxides of molybdenum, vanadium and/or tungsten and also tellurium oxide, wherein the catalyst being regenerated is impregnated with an aqueous solution or suspension containing a molybdenum, vanadium and/or tungsten compound and also a tellurium compound and then dried and calcined at from 400° to 850° C. This process has the disadvantage that the catalyst obtained is so finely divided as to be non-fluidizable and that it lacks firmness.

DE-C 28 48 850 describes a process whereby a spent metal oxide catalyst containing antimony and also at least one of the metals iron, cobalt, nickel, manganese, uranium, cerium, tin and/or copper is impregnated with an aqueous nitric acid solution and/or an aqueous solution of ammonium nitrate, an alkali or alkaline earth metal nitrate or a nitrate of metals such as iron, cobalt, nickel, copper, bismuth and/or tellurium and then dried and heated. This process too fails to convert a spent, mechanically damaged catalyst into a fluidizable catalyst.

DD Patent 371,997 describes a process whereby a spent catalyst containing one of the oxides of bismuth, molybdenum, iron and/or chromium with or without other elements is regenerated by first grinding the spent catalyst to a particle size of below 50 μm and then treating it with an aqueous salt solution or suspension of oxidic compounds of at least one of the elements bismuth, molybdenum, iron and/or chromium as reactivating solution at pH 0–3 and 20°–100° C., the amount of reactivating solution being such as to produce at the same time 5 times the amount of fresh catalyst, and then the total mixture is spray dried and heat treated. The process has the disadvantage that for every part by weight of spent catalyst it is necessary to prepare 5 parts of fresh catalyst. Nothing is discernible as to how a fluidizable catalyst of adequate mechanical stability might be obtainable from a spent catalyst alone.

It is an object of the present invention to make available regenerated metal oxide catalysts that are fluidizable, highly abrasion and fracture resistant, very efficient in converting propene and very selective in respect of the desired products.

We have found that this object is achieved by a process for regenerating deactivated metal oxide catalysts comprising at least one of the elements antimony, iron, bismuth, molybdenum, vanadium, tungsten and/or uranium and a peptizable carrier, comprising the steps of:

a) grinding the metal oxide catalyst in the presence of water to obtain an aqueous suspension of the metal oxide catalyst having a particle size of from 10 nm to 10 μm, b) heating the aqueous suspension of the metal oxide catalyst of stage a) to 30°–120° C. and adding an acid which peptizes the carrier, c) spray drying the acidic suspension of the metal oxide catalyst of stage b) to obtain fluidizable metal oxide catalyst particles, d) heating the fluidizable metal oxide catalyst particles of stage c) to 500°–850° C. to obtain a fluidizable metal oxide catalyst.

The present invention also provides regenerated catalysts obtainable by the abovementioned process.

The present invention further provides for the use of regenerated metal oxide catalysts obtainable by the abovementioned process for the amoxidation of olefins to the corresponding nitriles, the oxidation of olefins to the corresponding aldehydes or the oxidative dehydrogenation of olefins to diolefins and also the amoxidation of methyl-substituted aromatics to the corresponding nitriles.

The novel process has the advantage that the regenerated catalysts are highly abrasion and fracture resistant. It also has the advantage that the regenerated catalysts obtained give high conversions and make possible a high selectivity in respect of the desired end products. The catalysts prepared according to the invention are also notable for their excellent fluidizability. Finally, the novel process has the advantage that it dispenses with the need to dispose of spent catalysts, since it converts them into useful catalysts.

According to the invention, starting materials for stage a) comprise deactivated metal oxide catalysts comprising at least one of the elements antimony, iron, bismuth, molybdenum, vanadium, tungsten and/or uranium and also peptizable carriers. Such catalysts may also contain further catalytically active elements, e.g. elements of main groups 1, 2, 3, 5 and 6 and of subgroups 5 to 7 of the periodic table. Suitable peptizable carriers are for example aluminum oxide and silicon dioxide. Particular preference is given to silicon dioxide present in the catalyst in a finely divided form, derived for example from a sol. Peptizable for the purposes of the present invention denotes the formation of OH groups on the surface of a particle on treatment with an aqueous acid, which OH groups shall be capable of in turn forming a bond with the OH groups of an adjacent particle in the course of drying and calcination to form a strong bond within a larger assembly. The peptizable carrier content is advantageously from 20 to 80% by weight, based on the sum total of carrier and catalytically active metal oxide. In general, the spent catalysts will have an average particle size of from 1 to 100 μm, in particular of from 2 to 25 μm.

Such spent catalysts are obtained for example in the oxidative dehydrogenation of butane to butene, in the oxidative dehydrogenation of propene to acrolein, in the amoxidation of propene and of methyl-substituted aromatics to the corresponding nitriles, and in the oxidative dehydrogenation of olefins, preferably in a fluidized bed process.

Preferred catalysts are for example iron-bismuth-molybdenum oxide catalysts which may additionally contain at least one of the elements nickel, cobalt, magnesium, vanadium, tungsten, calcium, phosphorus, arsenic, antimony and/or an alkali metal and also optionally in addition at least one of the elements zinc, cadmium, boron, tungsten, yttrium, zirconium, silver, sulfur, cerium, thorium, chromium, tin, manganese, indium, copper, tantalum, tellurium and/or lanthanum. Suitable catalysts are described for example in German Patent 2,530,959.

Other preferred catalysts are antimony-irontellurium oxide catalysts which may additionally contain at least one of the elements cobalt, nickel, manganese, tin and/or copper and also at least one of the metals molybdenum, vanadium and/or tungsten plus at least one of the elements zinc, potassium, magnesium, aluminum, zirconium, bismuth, cerium, chromium, phosphorus and/or boron. Suitable catalysts are described for example in German Patent 2,560,480.

If the metal oxide catalysts to be regenerated additionally contain organic and inorganic contaminants, for example from quenching the amoxidation gases, it is advantageous to heat treat the catalysts with oxygen-containing gases, advantageously air, at from 300° to 700° C. before they are ground. Such contaminated metal oxide catalysts generally contain from 10 to 50% of unspecifiable organics with or without from 1 to 20% of ammonium sulfate. The oxidative treatment with gases containing molecular oxygen, such as air, at from 300° to 700° C. advantageously takes from half an hour to 30 hours, for example in a fluidized bed, in a rotary furnace or in a tunnel furnace.

The starting metal oxide catalysts are ground in the presence of water. The amount of water used is advantageously from 0.5 to 10 parts by weight per part by weight of metal oxide catalyst. The grinding is advantageously carried out in a stirred ball mill. The result is a suspension of metal oxide catalyst in water in which the particle size of the ground metal oxide catalyst is from 10 nm to 10 $\mu$m, in particular from 10 nm to 2 $\mu$m. It is particularly advantageous for the average particle size to be from 50 nm to 1 $\mu$m.

Prior to further processing the aqueous suspension of metal oxide catalyst it is advantageous to add to the suspension an aqueous ammonia solution, for example from 10 to 80% by weight of $NH_3$ in strength, and/or the solution of an ammonium salt with a decomposable acid, for example nitric acid, acetic acid, formic acid or oxalic acid, in particular nitrate. The concentration of $NH_4^+$ ions per liter should advantageously be from 10 to 200 g. It is advantageous to maintain a temperature of from 30° to 102° C., for example for a period of from 15 to 120 minutes.

In stage b), the aqueous suspension of the metal oxide catalyst of stage a) is heated to 30°–120° C. and has added to it at least one acid which is capable of peptizing the catalyst carrier.

Suitable acids are for example sulfuric acid, nitric acid, acetic acid, formic acid, glutaric acid and oxalic acid. It is particularly advantageous to use nitric acid. The amount of acid added is advantageously such as to produce a strongly acid solution, for example a solution with a pH of from 0 to 3. In general, from 0.01 to 10 parts by weight of acid will be used per part by weight of suspended metal oxide catalyst. It is advantageous to maintain a temperature of from 30° to 120° C. for a period of from 15 to 120 minutes.

It is advantageous to add metal salts to the suspension in stage a) or b), for example nitrates of at least one of the elements already present in the catalyst which are to be replenished, in an amount which is sufficient to achieve replenishment. It is advantageous to add for example nitrates or other compounds of antimony, iron, cobalt, nickel, manganese, copper, molybdenum, tungsten or tellurium or the metals themselves. In particular, the levels of volatile molybdenum and tellurium are replenished. In addition, it is also possible to modify the catalyst in some way by the addition of further elements, for example by the addition of lanthanum, cerium, chromium, zinc or phosphoric acid or of heteropoly acids of phosphoric acid, silica and tungstic acid in catalytically active amounts.

If no ammonia or ammonium nitrate was added in stage a), it is advantageous to add ammonium nitrate or salts of other decomposable acids such as formic acid, acetic acid or oxalic acid, in particular ammonium nitrate, in stage b), advantageously in an amount of from 5 to 500 g of ammonium ions per liter.

It has been found to be advantageous to adjust the suspension to a pH of from 5 to 0.5, advantageously from 0 to 3, in particular from 1 to 2.5, by adding aqueous ammonia before the suspension is processed in the next stage. The suspension is advantageously stirred at from 40 ° to 80° C. for a further 15–60 minutes.

The acidic suspension of metal oxide catalyst obtained in stage b) is spray dried in stage c) to obtain a fluidizable precursor of the metal oxide catalyst. The particles obtained advantageously have an average particle size of 50 $\mu$m±20.

The fluidizable metal oxide catalyst particles obtained in stage c) are then calcined in stage d) at from 500° to 850° C., advantageously for a period of from 0.5 to 10 hours. It is particularly advantageous to carry out the calcination in two stages, for example in a first stage of from 0.5 to 10 hours to decompose ammonium salts, for example at from 150° to 400° C., and in a second stage at from 500° to 850° C.

The regenerated metal oxide catalysts obtainable according to the invention are notable for excellent abrasion resistance, for example from 0.5 to 2 g/kg of catalyst/h in a jet mill.

The catalysts obtainable according to the invention are suitable for the oxidative dehydrogenation of olefins, for the preparation of acrolein from propene, in particular for the amoxidation of propene or methyl-substituted aromatics to the corresponding nitriles.

The amoxidation of propene to acrylonitrile is advantageously carried out by reacting propene with gases containing molecular oxygen, such as air, in excess and also ammonia and optionally steam over a fluidized metal oxide catalyst as specified above at from 300° to 500° C. under superatmospheric pressure, for example at from 1 to 4 bar.

The invention will now be more particularly described by way of example.

EXAMPLE 1

A recovered catalyst of the composition $Fe_{10}Sb_{2.5}Te_{1.0}W_{0.25}O_{68}(SiO_2)_{30}$ which contained 40% by weight of organics and 10% by weight of ammonium sulfate and had a particle size such that two thirds of the mass had a diameter of about $<16$ $\mu$m and one third of the mass had a diameter $>16$ $\mu$m was heated in a rotary furnace under air at 500° C. for 5 hours. The catalyst thus obtained had an organics and ammonium sulfate content of less than 1% by weight.

The metal oxide catalyst thus pretreated was comminuted with 1.5 parts of water in a stirred ball mill to an average particle size of 550 nm. The resulting suspension was treated with 2 parts by weight of 23% by weight aqueous nitric acid per part by weight of catalyst, heated to 50° C. and stirred for 30 minutes. The suspension was then brought to pH 2 with aqueous ammonia solution and stirred at 50° C. for a further 30 minutes.

The suspension thus obtained was then spray dried and then calcined at 720° C. for 3 hours. The catalyst particles obtained had an average diameter of 50 μm.

1000 parts by weight of the catalyst thus obtained were fluidized per hour with 6350 parts by volume (based on standard conditions) of a gas mixture of propene, ammonia and air. The gas mixture had a molar ratio of air to propene of 12 and a molar ratio of ammonia to propene of 1.2. The temperature in the fluidized bed was 460° C. and the pressure was 1 bar. The exit gas from the reactor was analyzed by gas chromatography to determine the selectivity in respect of acrylonitrile formation and the conversion of the propene. The propene conversion was found to be 98% and the acrylonitrile yield 77.5%. The catalyst particles were as round and abrasion resistant as fresh catalyst particles, the only difference being that the diameter had changed from 51 μm to 50 μm.

EXAMPLE 2

Example 1 was repeated, except that the catalyst was not ground. The catalyst particles obtained were not round and had a size dimension of 62 μm. On fluidization the catalyst rapidly turned to fine dust and could not be used.

We claim:

1. A process for regenerating deactivated iron containing oxide catalysts additionally containing either I.
   - a1) antimony and tellurium and at least one of the elements
   - b1) molybdenum, tungsten, vanadium, copper or II.
   - a2) bismuth and molybdenum and at least one of the elements
   - b2) K, Rb, Cs, Cr, Mn or P comprising steps of:

a) grinding the metal oxide catalyst in the presence of water to obtain an aqueous suspension of the metal oxide catalyst having a particle size of from 10 nm to 10 μm,
   b) heating the aqueous suspension of the metal oxide catalyst of stage a) to 30°–120° C. and adding an acid which peptizes the carrier,
   c) spray drying the acidic suspension of the metal oxide catalyst of stage b) to obtain fluidizable metal oxide catalyst particles, and
   d) heating the fluidizable metal oxide catalyst particles of stage c) to 500°–850° C. to obtain a fluidizable metal oxide catalyst.

2. A process as defined in claim 1, wherein, in stage a), the metal oxide catalyst is comminuted to an average particle size of from 10 to 1000 nm.

3. A process as defined in claim 1, wherein aqueous ammonia or ammonium nitrate is added to the suspension in stage (a) or (b).

4. A process as defined in claim 1, wherein nitric acid is added in stage b).

5. A process as defined in claim 1, wherein per part by weight of metal oxide catalyst from 0.01 to 10 parts by weight of acid are added in stage b).

6. A process as defined in claim 1, wherein additionally at least one of the elements Mo, Sb or Te is added in stage a) or b).

7. A process as defined in claim 1, wherein, following stage b), ammonia is added to the aqueous suspension to a pH of from 5 to 0.5.

8. A process as defined in claim 1, wherein the metal oxide catalyst contains silicon dioxide and/or aluminum oxide as carrier.

9. A process as defined in claim 1, wherein the metal oxide catalyst used contains the oxides of antimony, iron and tellurium and also at least one of the elements, molybdenum, tungsten, vanadium or copper.

10. A process as defined in claim 1, wherein the metal oxide catalyst used contains the oxides of bismuth, molybdenum and iron and also at least one of the elements K, Rb, Cs, Cr, Mn or P.

11. A process as defined in claim 1, wherein, prior to stage a), the metal oxide catalyst is heated to 300°–700° C. under a gas containing molecular oxygen.

* * * * *